US012201676B2

(12) United States Patent
Duelo Riu et al.

(10) Patent No.: US 12,201,676 B2
(45) Date of Patent: *Jan. 21, 2025

(54) COMPOSITION COMPRISING DIAMINE OXIDASE FOR USE IN THE TREATMENT OR PREVENTION OF FIBROMYALGIA OR CHRONIC FATIGUE SYNDROME

(71) Applicant: DR HEALTHCARE ESPAÑA, S.L., Barcelona (ES)

(72) Inventors: Carlos Duelo Riu, Barcelona (ES); Juan José Duelo Riu, Barcelona (ES)

(73) Assignee: DR HEALTHCARE ESPAÑA, S.L. (ES)

( * ) Notice: Subject to any disclaimer, the term of this patent is extended or adjusted under 35 U.S.C. 154(b) by 97 days.

This patent is subject to a terminal disclaimer.

(21) Appl. No.: 15/283,778

(22) Filed: Oct. 3, 2016

(65) Prior Publication Data

US 2017/0020993 A1    Jan. 26, 2017

Related U.S. Application Data

(63) Continuation-in-part of application No. 14/005,020, filed as application No. PCT/IB2012/051276 on Mar. 16, 2012, now abandoned.

(30) Foreign Application Priority Data

Mar. 18, 2011   (ES) ................. ES201130383

(51) Int. Cl.
| | |
|---|---|
| *A61K 38/44* | (2006.01) |
| *A61K 9/00* | (2006.01) |
| *A61K 9/20* | (2006.01) |
| *A61K 9/50* | (2006.01) |
| *A61K 31/522* | (2006.01) |
| *A61P 21/02* | (2006.01) |
| *A61P 25/06* | (2006.01) |
| *A61K 9/48* | (2006.01) |

(52) U.S. Cl.
CPC ............ *A61K 38/44* (2013.01); *A61K 9/0095* (2013.01); *A61K 9/2054* (2013.01); *A61K 9/2077* (2013.01); *A61K 9/5026* (2013.01); *A61K 31/522* (2013.01); *C12Y 104/03022* (2013.01); *A61K 9/4825* (2013.01)

(58) Field of Classification Search
CPC .......... A61K 38/44; A61P 43/00; A61P 25/00; A61P 25/28; A61P 29/00; A61P 19/02; A61P 25/06; A61P 25/02; A61P 21/02; A61P 21/00

See application file for complete search history.

(56) References Cited

U.S. PATENT DOCUMENTS

| | | |
|---|---|---|
| 3,721,733 A | 3/1973 | Van Leeuwen |
| 4,703,045 A | 10/1987 | Guinot |
| 4,725,540 A | 2/1988 | Underberg et al. |
| 4,851,243 A | 7/1989 | Andersen et al. |
| 8,003,343 B2 | 8/2011 | Missbichler et al. |
| 9,795,654 B2 * | 10/2017 | Duelo Riu et al. ..... A61K 38/44 |
| 2006/0002913 A1 | 1/2006 | Gehlsen |
| 2008/0193491 A1 | 8/2008 | Missbichler et al. |
| 2008/0227116 A1 | 9/2008 | Missbichler et al. |
| 2008/0306066 A1 | 12/2008 | Carruthers et al. |
| 2010/0330191 A1 | 12/2010 | Missbichler et al. |
| 2011/0236491 A1 | 9/2011 | Chantalat et al. |
| 2013/0344136 A1 | 12/2013 | Duelo Riu et al. |
| 2013/0344137 A1 | 12/2013 | Duelo Riu et al. |
| 2014/0004179 A1 | 1/2014 | Duelo Riu et al. |
| 2014/0004180 A1 | 1/2014 | Duelo Riu et al. |
| 2015/0093430 A1 | 4/2015 | Duelo Riu et al. |
| 2016/0024481 A1 | 1/2016 | Duelo Riu et al. |

FOREIGN PATENT DOCUMENTS

| | | |
|---|---|---|
| EP | 0132674 A2 | 2/1985 |
| EP | 0865737 A2 | 9/1998 |
| EP | 1277477 A2 | 1/2003 |
| EP | 2020446 A1 | 2/2009 |
| ES | 2132037 A1 | 8/1999 |
| ES | 2387973 B1 | 10/2013 |
| ES | 2388395 B1 | 10/2013 |
| ES | 2388515 B1 | 10/2013 |
| FR | 2101095 A1 | 3/1972 |
| FR | 2215944 A1 | 8/1974 |
| GB | 1313318 A | 4/1973 |
| WO | WO-9207475 A1 | 5/1992 |
| WO | WO-9631130 A2 | 10/1996 |
| WO | WO-0243745 A2 | 6/2002 |
| WO | WO-200243745 A2 | 6/2002 |
| WO | WO-03/035000 A2 | 5/2003 |
| WO | WO-2006003213 A1 | 1/2006 |

(Continued)

OTHER PUBLICATIONS

Taylor, "Quality of life and symptom severity for individuals with chronic fatigue syndrome: Findings from a randomized clinical trial," American Journal of Occupational Therapy, vol. 58, No. 1, pp. 35-43 (Year: 2004).*

Buskila et al, "Biology and therapy of fibromyalgia. Genetic aspects of fibromyalgia syndrome," Arthritis Research & Therapy, vol. 8, No. 5, 218, pp. 1-5 (Year: 2006).*

Shin et al, "Inhibitory effect of anaphylactic shock by caffeine in rats," International Journal of Immunopharmacology, vol. 22, No. 6, pp. 411-418 (Year: 2000).*

White et al, "Classification, Epidemiology, and Natural History of Fibromyalgia," Current Pain and Headache Reports, vol. 5, No. 4, pp. 320-329 (Year: 2001).*

Cozza, S.J. et al.; "Treatment of Children and Adolescents"; Clinical Psychiatric Treatment, vol. II, Chapter XXXIII; 2004; p. 1408.

(Continued)

*Primary Examiner* — Tracy Liu
(74) *Attorney, Agent, or Firm* — Shackelford, McKinley & Norton, LLP

(57) ABSTRACT

A composition includes diamine oxidase for use in prevention or treatment of symptoms and disorders caused by fibromyalgia or chronic fatigue syndrome.

7 Claims, No Drawings

(56) References Cited

FOREIGN PATENT DOCUMENTS

| WO | WO-2007/144153 A2 | 12/2007 |
|---|---|---|
| WO | WO-2008/113871 A1 | 9/2008 |
| WO | WO-2012127381 A1 | 9/2012 |
| WO | WO-2012127391 A1 | 9/2012 |
| WO | WO-2012127392 A1 | 9/2012 |

OTHER PUBLICATIONS

Tallgren, Antti, "International Search Report" prepared for PCT/IB2012/051276, as mailed Jun. 9, 2012, 6 pages.

Maintz, Laura, et al., "Histamine and histamine intolerance", The American Journal of Clinical Nutrition, American Society for Nutrition, U.S., May 1, 2007, vol. 85, No. 5, pp. 1185-1196.

Tallgren, Antti,"International Search Report", prepared for PCT/IB2012/051253 as mailed Jul. 6, 2012, 4 pages.

Tallgren, Antti, "International Search Report" for PCT/IB2012/051252, as mailed Jul. 6, 2012, 4 pages.

Zimmerman, "Pathophysiological Mechanisms of Fibromyalgia," The Clinical Journal of Pain, vol. 7, No. 1, pp. S8-S15, (1991).

Meggs, "Neurogenic Switching: a Hypothesis for a Mechanism for Shifting the Site of Inflammation in Allergy and Chemical Sensitivity Environmental Health Perspectives," vol. 103, No. 1, pp. 54-56, (1995).

Arnold et al., "Family Study of Fibromyalgia," Arthritis & Rheumatism, vol. 50, No. 3, pp. 944-952, (2004).

Van Ittersum et al., "Illness Perceptions in Patients with Fibromyalgia," Patient Education and Counseling, vol. 74, Issue 1, pp. 53-60, (2009).

Mason et al., "Evaluation of a Multimodal Treatment Program for Fibromyalgia," Journal of Behavioral Medicine, vol. 21, No. 2, pp. 163-178, (1998).

Vaerøy et al., "Treatment of Fibromyalgia (Fibrositis Syndrome): a Parallel Double Blind Trial with Carisoprodol, Paracetamol and Caffeine (Somadril Comp®) Versus Placebo," Clinical Rheumatology, vol. 8, Issue 2, pp. 245-250, (1989).

Biofunctionalism.com, "Fibromyalgia and DAO Deficiency," http://biofunctionalism.com/fibromyalgia-and-dao-deficiency/, Oct. 11, 2010, 3 pages.

Dechene, L.; "Chronic Fatigue Syndrome: Influence of Histamine, Hormones and Electrolytes"; Medical Hypothesis, vol. 40, No. 1; Jul. 1992; pp. 55-60.

John, Joshi, et al.; "Caffeine Promotes Glutamate and Histamine Release in the Posterior Hypothalamus"; Am J Physiol Regul Integr Comp Physiol, vol. 307; Jul. 16, 2014; pp. R704-R710.

Grozman, M., et al.; "Change in Serum Histamine Indexes in Calves under the Influence of Caffeine"; Trudy Moldavskoi Ovoshchekartofel'noi Orositel'noi Opytnoi Stantsii (1971), 7, 277-80 (Abstract only).

Roth, J.A., et al.; "The Effect of Vagotomy and Atropine upon Caffeine Stimulation of Gastric Secretion"; Gastroenterology (1945), 5, 129-34 (Abstract only).

Stoltner, Anton, "International Search Report" for PCT/IB2012/051275, as mailed May 21, 2012, 3 pages.

Shimoda, et al., "Investigation of the mechanism of alcohol-induced bronchial asthma", Journal of Allergy and Clinical Immunology, Mosby, Inc, US, Jan. 1, 1996, vol. 97, No. 1, pp. 74-84.

Linneberg, A., et al., "Genetic determinants of both ethanol and acetaldehyde metabolism influence alcohol hypersensitivity and drinking behaviour among Scandinavians", Clinical & Experimental Allergy, Wiley Interscience, Jan. 1, 2010, vol. 40, No. 1, pp. 123-130.

Pittler, Max H., et al.; "Interventions for Preventing or Treating Alcohol Hangover: Systematic Review of Randomised Controlled Trials"; BJM, vol. 331; Dec. 22, 2005; 4 pages.

Stephens, Richard, et al.; "A Review of the Literature on the Cognitive Effects of Alcohol Hangover"; Alcohol & Alcoholism, vol. 43, No. 2; Jan. 31, 2008; pp. 163-170.

Swift, Robert, et al.; "Alcohol Hangover: Mechanisms and Mediators"; Alcohol Health & Research World, vol. 22, No. 1; Jan. 1998; pp. 54-60.

Stoltner, Anton, "International Search Report," prepared for PCT/IB2013/053068, as mailed Aug. 13, 2013, four pages.

Wigal, Sharon B., "Efficacy and Safety Limitations of Attention-Deficit Hyperactivity Disorder Pharmacotherapy in Children and Adults," CNS Drugs 2009; 23 Suppl. 1, 2009, pp. 21-31.

Brown, Ronald T. et al., "Treatment of Attention-Deficit/Hyperactivity Disorder: Overview of the Evidence," Pediatrics vol. 115, No. 6, Jun. 6, 2005, pp. e749-e757.

Montañés-Rada, F., et al., "Fármacos para el trastorno por déficit de atención/hiperactividad," Rev Neurol 2009; 48(9), Mar. 31, 2009, pp. 469-481.

Howard, Harry R.; "Agents for Attention-Deficit Hyperactivity Disorder—An Update"; Expert Opinion on Therapeutic Patents, Informa Healthcare, GB; vol. 14, No. 7; Jul. 1, 2004; pp. 983-1008.

Stevenson, Jim, et al.; "The Role of Histamine Degradation Gene Polymorphisms in Moderating the Effects of Food Additives on Children's ADHD Symptoms"; Am J Psychiatry 167:9; Sep. 2010; pp. 1108-1115.

Bodmer, S., et al.; "Biogenic Amines in Foods: Histamines and Food Processing"; Inflammation Research, vol. 48, No. 6; Jun. 1999; pp. 296-300.

National Fibromyalgia & Chronic Pain Association, "What is Fibromyalgia?" National Fibromyalgia & Chronic Pain Association, "What is Fibromyalgia?," URL: <https://www.fmcpaware.org/fibromyalgia/about-fm.html>, Retrieved: Aug. 10, 2018, 3 pages.

Work Wellness and Disability Prevention Institute (WWDPI); "Fibromyalgia"; https://www.wwdpi.org/ChronicDisease/HealthTopics/MusculoskeletalDisorders/Pages/Fibromyalgia.aspx; last updated Jun. 12, 2018; 7 pages.

Centers for Disease Control and Prevention; "Myalgic Encephalomyelitis/Chronic Fatigue Syndrome"; https://www.cdc.gov/me-cfs/index.html; last updated Jun. 29, 2018; 4 pages.

WebMD, Migraine & Headaches Center: Physician Reviewed Headache Information, https://www.webmd.com/migraines-headaches/default.htm. Retrieved: Nov. 15, 18; 5 pages.

Ibuprofen—NHS, https://www.nhs.uk/conditions/ibuprofen/. Last reviewed: May 17, 2016; Retrieved: Nov. 15, 2018, 9 pages.

Migraine—definition of migraine by The Free Dictionary, https://www.thefreedicitionary.com/migraine. Retrieved: Nov. 15, 2018; 4 pages.

Silent Migraine, https://migraine.com/migraine-types/silent-migraine/ Written by Otesa Miles, Last reviewed: Aug. 2014, Retrieved: Nov. 15, 2018; 5 pages.

* cited by examiner

COMPOSITION COMPRISING DIAMINE OXIDASE FOR USE IN THE TREATMENT OR PREVENTION OF FIBROMYALGIA OR CHRONIC FATIGUE SYNDROME

CROSS-REFERENCE TO RELATED APPLICATIONS

This patent application is a continuation-in-part patent application of U.S. patent application Ser. No. 14/005,020, which is a national-stage filing of International Patent Application No. PCT/IB2012/051276. U.S. patent application Ser. No. 14/005,020 is incorporated by reference.

DESCRIPTION

Field of the Invention

The present invention refers to a composition comprising diamine oxidase (DAO) for use in the treatment or prevention of fibromyalgia or chronic fatigue syndrome.

BACKGROUND OF THE INVENTION

Fibromyalgia (etymologically the term is derived from the Latin and Greek: pain of the muscle of the connective tissue) is defined as a group of symptoms and musculoskeletal disorders that are fundamentally characterised by extreme fatigue, persistent pain, variable amount of stiffness of the muscles, tendons and surrounding soft tissue and a wide range of other psychological symptoms such as sleep difficulties, morning stiffness, headaches and memory problems (the so-called "memory lapses") that often prevent routine functioning of the subject.

Overall prevalence is 2.37%, affecting mostly women (in a proportion between 8/1 and 20/1), particularly younger women between 20 and 50 years of age.

Diagnosis is controversial owing to the absence of abnormalities found in physical examination, target laboratory examinations or studies of medical images for diagnostic confirmation. Its origin is due to abnormalities in the central nervous system affecting brain regions that may be linked to the clinical symptoms.

The main characteristic of fibromyalgia is diffuse and generalised musculoskeletal pain or prominent stiffness that affects at least 3 anatomical locations for over 3 months,[ ] without which the disorder cannot be diagnosed. The pain is usually intense and often difficult to describe, and in general gets worse with intense physical exercise, cold and emotional stress.

The locations where the symptoms of fibromyalgia often appear are the lumbar region (lower back), neck, thorax and thighs. The disorder of the muscles refers to a painful and localised cramp that is sometimes associated with other problems (for example pregnancy). Sometimes, localised muscle spasm is observed.

Other additional symptoms may include urinary incontinence, headache, migraines, abnormal periodic movements of the extremities (paroxysmal movements), especially of the feet (trigger leg syndrome), difficulty in concentrating and difficulty in remembering things (poor memory); also common is an increase in tactile sensitivity, generalised itching, dry eyes and mouth, hum and ringing in the ears (tinnitus), visual disturbances (phosphene) and some neurological symptoms of lack of motor coordination. Raynaud's phenomenon has been associated as a clinical manifestation occasionally found during the course of this disease.

Between 70% and 90% of those suffering from fibromyalgia also report sleep disorders, expressed as a non-refreshing, light and unstable sleep. A heterogeneous group of symptoms are often additionally associated including severe (adynamia) and even incapacitating (asthenia) weakness, disorders of the intestinal rhythm, stiffness in upper or lower extremities and, very frequently, depressive episodes accompanied by panic attacks. Sleep disorders are very common in patients with this pathology. These disorders basically consist of frequent nightmares, non-refreshing sleep, which can be the cause of a disorder known as diurnal hypersomnia, and a high number of painful discharges in the muscles during sleep.

Extreme fatigue is present in all activities carried out by people with fibromyalgia, so everyday tasks are inevitably impeded. Depending on the seriousness and of the variation in degree, this tiredness can range from bearable to being an almost insurmountable disability limiting tasks both at home and at work.

Related to this tiredness, as a causal or aggravating condition, is poor quality of sleep, which prevents those with this disorder from having a refreshing sleep and, consequently, prevents rest, which accentuates tiredness and fatigue in the future.

With respect to treatment, it is thought that there is currently no cure for fibromyalgia and the treatments leading to relief from the symptoms require the intervention of a multidisciplinary team. The treatments used include antidepressives, muscle relaxants, serotonin inhibitors, NSAIDs, etc. In addition, rehabilitation, trigger point (myofascial) massage, craniosacral therapy, chiropractic treatment, osteopathy, stretching exercises and/or aerobics, alternative medicine, posture training, occupational therapy, relaxation therapy, behavioural therapy, nutrition, acupuncture, etc. are considered suitable.

Chronic fatigue syndrome is a disease considered by the WHO as a serious neurological disease that can progressively affect the immune, neurological and cardiovascular and endocrine systems. It is characterised by manifestations including severe fatigue, feverishness or fever, non-refreshing sleep, intolerance to light, sound and temperature changes, muscular pain and pain in the joints, multiple chemical sensitivities, electromagnetic sensitivity, sensitivity to other environmental factors, sensation of permanent flu, chronic faringitis, substantial loss of concentration and memory, spatial disorientation, intolerance to emotional stress and physical activity.

The symptomotology is very variable in terms of severity and temporal presentation, ranging from states of prolonged abnormal fatigue with various flu-like symptoms to a very severe chronic disease with many symptoms that can affect the whole body and put the patient in bed for very long periods of time, even leading to a complete inability to carry out any activity for years.

In severe cases, all the following symptomotology may be present: very profound exhaustion, generalised pain, feeling of weakness at the slightest physical, mental or emotional effort, insomnia, etc.

Currently, it is estimated that the disease affects around 0.5% of the world population and that the proportion by gender is nine women to one man.

Currently, there is no effective medical treatment, either for fibromyalgia or for chronic fatigue.

Musculoskeletal pain common in people suffering from fibromyalgia and chronic fatigue, as well as other additional symptoms of both diseases, result from dilation of the blood vessels by the effect caused by some vasodilator substances, mainly histamine, in the body and by the accumulation of histamine in muscle tissue. Thus histamine has a direct effect in the various manifestations of pain, common in people suffering from fibromyalgia and chronic fatigue, with a key role in the pain processes.

Histamine [2-(4-imidazolyl)ethylamine] is an important mediator of many biological processes including inflammation, secretion of gastric acid, neuromodulation and the regulation of the immune function. Due to its potent pharmacological activity, even at very low concentration, it is necessary to regulate the synthesis, transport, storage, release and degradation of histamine very carefully in order to avoid undesirable reactions. High concentrations of free histamine in the circulation have been described to lead to undesirable effects such as headache, blocked nose or rhinorrhoea, obstruction of respiratory pathways, tachycardia, gastric and intestinal pains, eyelid swelling, cutaneous erythema, reduction of arterial pressure, bronchospasms, etc.

Histamine is produced by human beings and stored in an inactive form in the metachromatic granules of the mast cells and basophilic leukocytes, where it is available for immediate release. The highest concentrations of histamine are measured in the lungs. After release, histamine becomes an extraordinary powerful mediator of a large number of physiological and pathophysiological processes, frequently by interaction with the cytokines.

Histamine can also enter the human body from the outside as it is generated by microbiological action in the course of processing foods and, consequently, is present in substantial quantities in many fermented foods and drinks such as wine, champagne and a large proportion of alcoholic drinks.

Therefore after ingesting certain foods, a significant increase in circulating histamine is produced.

The main route of inactivation of ingested histamine is oxidative deamination of the primary amino group, catalysed by diamine oxidase (DAO) to produce imidazole acetaldehyde.

The main function of DAO is to prevent histamine ingested with food from reaching the blood circulation from the intestine.

In addition to histamine, DAO can degrade other biogenic amines such as, for example, putrescine, spermidine and cadaverine. It has a molecular weight of approximately 182 kDa and a carbohydrate ratio of 11%. It belongs to the copper-containing amine oxidase class that catalyses oxidative deamination of primary amines to give aldehydes, ammonia and hydrogen peroxide. DAO uses molecular oxygen for the oxidative deamination of histamine to imidazole acetaldehyde, ammonia and hydrogen peroxide.

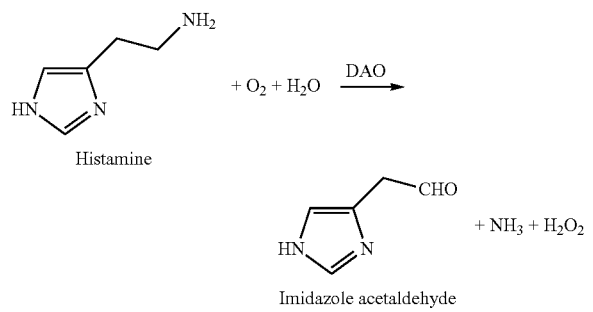

DAO is mainly found in the small intestine, liver, kidneys and blood leukocytes. The level of DAO in the blood of pregnant women is approximately 500 to 1000 times higher than of non-pregnant women as DAO in pregnant women is additionally formed in the placenta. Histamine is continually produced in humans and is excreted via the intestine, being degraded on passing through intestinal mucosa by the DAO found there.

DAO is a sensitive enzyme that can be inhibited by different substances such as other biogenic amines, alcohol and by its degradation product acetaldehyde, as well as by various medicinal drugs.

In addition to inhibition of DAO by certain types of substances, there is a significant percentage of the population in which blood DAO levels are anomalously low, which leads to levels of histamine in blood being at higher levels than considered normal (2-20 micrograms/0.1 L). A series of pathologies appear in these types of subject caused by high levels of blood histamine.

In this situation, preventative administration and treatment of supplementary amounts of DAO contributes to degradation of the excess histamine.

Patent EP 132674 describes a procedure for the enzymatic separation of free amines in foods containing a high amine content such as chocolate, cheese, especially mature, salami, wine and yeast extracts by the use of amine oxidase enzymes, particularly DAO, obtained from *Aspergillus niger*, in the presence of molecular oxygen. The presence of these free amines in certain foods is thought to cause migraines.

U.S. Pat. No. 4,725,540 describes a procedure for preparing DAO from a microorganism that makes it such as *Candida crusei* or a bacterium that produces lactic acid in a nutrient medium so that the DAO produced is capable of degrading histamine at a pH of between neutral and approximately 4.

Patent application WO 02/43745 from 2001 describes the systematic use of DAO of plant origin for the treatment of diseases mediated by histamine, particularly for the treatment of allergies in general and anaphylactic reactions in particular. There are also pharmaceutical compositions comprising DAO as the active ingredient, including corresponding dosages and administration protocols. The DAO used originates from plants. There is no mention of the possible use of DAO compositions for the prevention and treatment of fibromyalgia or of chronic fatigue syndrome.

Patent application WO 2006003213 of 2005 refers to pharmaceutical compositions for the treatment of histamine-induced diseases comprising DAO of animal origin where the composition is presented in a form protected against gastric acid for oral or peroral administration. The compositions are particularly directed for the treatment of urticaria, atopic dermatitis and scombrotoxic poisoning. This patent application favours the use of DAO of non-plant origin because it is argued that this form has the advantage that allergens present in plants do not have a negative effect on the administration of DAO, as allergens essentially promote the release of endogenous histamine. The DAO used is preferably obtained from pig kidneys or by recombinant techniques. There is no mention of the possible use of DAO compositions for the prevention and treatment of fibromyalgia or of chronic fatigue syndrome.

The present invention is focused on the treatment or prevention of fibromyalgia or of chronic fatigue syndrome by administering DAO, preferably fibromyalgia.

Fibromyalgia (FM) is a disease of unknown etiology characterized by chronic widespread pain that the patient locates in the locomotor system. Besides pain, other symptoms such as intense fatigue, sleep disturbances, paraesthesias in extremities, depression, anxiety, joint stiffness, headaches and feeling of swelling in hands, are other common clinical manifestations.

FM, defined by the ACR criteria for classification (American College of Rheumatology), is frequent in Spain with a prevalence of 2.4% of the general population older than 20 years, according to an EPISER study. In absolute numbers, around 700,000 patients are affected by FM in Spain. By gender, the prevalence among men is estimated at 0.2% against 4.2% in women, which implies a relation women/men of 21:1.

In the last few years, FM has become more important and currently is a major public health problem given its high prevalence, the lack of knowledge about causes and mechanisms, the absence of a curative treatment and the dissatisfaction of patients and professionals. This all leads to a series of consequences in health, economic and social levels.

Most recent data also indicates that in patients with FM, there is an alteration of the mechanisms of pain processing, probably caused by an imbalance in neuromodulators of the central nervous system.

On the other hand, concepts like histamine intolerance or food histaminosis have been highlighted repeatedly in recent years. Both concepts make reference to the accumulation of histamine in the organism resulting in different symptoms: migraine, headaches, general pain, gastrointestinal symptoms, dry skin, pruritus, fatigue, etc. Paradoxically, these symptoms are common in diseases such as fibromyalgia.

Definitions

"DAO" is the abbreviation used for the enzyme diamine oxidase responsible for catalysing the oxidative deamination of the primary amine group of histamine to give imidazole acetaldehyde. It is responsible for the main route of histamine inactivation.

"Fibromyalgia" is a group of musculoskeletal symptoms and disorders fundamentally characterised by:
  extreme fatigue
  persistent pain
  stiffness of variable intensity of muscles, tendons and surrounding soft tissue
  a wide range of other psychological symptoms such as difficulty in sleeping, morning stiffness, headaches and memory problems (so-called "memory lapses") that prevent routine functioning of the subject "Chronic fatigue" is the feeling of intense and prolonged tiredness or exhaustion (fatigue) that is not relieved with rest, the symptoms of which are similar to the majority of most common viral diseases (muscle pains, headache and fatigue). These symptoms may appear in a few hours or days and may last six months or more.

"Non-plant origin" means all those DAO that are not obtained from plants but from animal organisms or from other non-plant organisms. Thus all DAO isolated from living things falls under this definition.

"Plant origin" means all those DAO that are obtained from plant organisms.

"Biotechnological origin" means all those DAO that are recombinantly prepared from cell cultures or in non-vegetable organisms of any type where the DNA for DAO has been isolated.

"Prevention" means avoiding the appearance of symptoms and disorders that involve any type of pain caused by fibromyalgia or chronic fatigue.

"Treatment" means clinical intervention with the intent to change the natural course of fibromyalgia or chronic fatigue and is carried out during the course of the clinical pathology. The desirable effects of treatment include relief from symptoms, reduction of any direct or indirect pathology of the disease, reduction of the speed of progression of the disease, improvement or partial cure of the pathological status and remission or improved prognosis, as well as prevention of recurrence of the disease.

SUMMARY

The problem solved by the present invention is the treatment and prevention of the symptoms involving any kind of pain and of the symptoms and disorders that characterise fibromyalgia or chronic fatigue syndrome, preferably fibromyalgia.

Until the present invention, the relation between the symptoms of fibromyalgia or chronic fatigue and the accumulation of histamine had not been described. Therefore, no attempt had been made to treat the symptoms by treatment with DAO. The surprising effect of the present invention is that the administration of DAO reduces the concentration of histamine in blood and this leads to a significant improvement of the symptoms and disorders characterising fibromyalgia and chronic fatigue syndrome, preferably fibromyalgia.

The first aspect of the present invention, then, is the use of DAO in the preparation of a composition for the prevention or treatment of the symptoms and disorders caused by fibromyalgia or chronic fatigue, preferably fibromyalgia, or, alternatively, a composition comprising DAO for use in the prevention or treatment of the symptoms and disorders caused by fibromyalgia or chronic fatigue, preferably fibromyalgia.

The second aspect of the present invention is the use of DAO associated with caffeine for the preparation of a composition for the prevention or the treatment of the symptoms and disorders caused by fibromyalgia or chronic fatigue, preferably fibromyalgia, particularly of the symptoms of fibromyalgia derived by the arterial vasodilation produced by histamine, or alternatively, the composition comprising DAO further comprising caffeine for use in the prevention or the treatment of the symptoms and disorders caused by fibromyalgia or chronic fatigue, preferably fibromyalgia, particularly of the symptoms of fibromyalgia derived by the arterial vasodilation produced by histamine.

The third aspect of the present invention is oral DAO formulations, optionally containing caffeine, in the form of tablets, capsules and sachets.

The fourth aspect of the present invention are oral formulations of DAO prepared from free DAO, in powder, lyophilised powder, microcapsules, nanocapsules or liposomes containing DAO and optionally caffeine.

The fifth aspect of the present invention are oral formulations of DAO prepared from free DAO, in powder, lyophilised powder, microcapsules, nanocapsules or gastroprotected liposomes containing DAO and optionally also caffeine.

In a further aspect, the administration of the composition of the present invention is carried out together with a diet low in histamine-rich and/or histamine releasing food.

DETAILED DESCRIPTION OF THE INVENTION

A first aspect is the use of oral compositions comprising DAO for the preparation of a composition for the prevention or treatment of the symptoms and disorders caused by fibromyalgia or chronic fatigue syndrome, preferably fibromyalgia.

The DAO used in the present invention can be either of biotechnological origin or extracted from animals or plants.

If the DAO used is of non-plant origin, it is preferably in the form of a lyophilised powder. If the DAO used is of plant origin, it may also be in liquid form.

The different compositions comprising DAO to be used in the preparation of a composition for the prevention or treatment of symptoms or disorders caused by fibromyalgia or chronic fatigue syndrome, preferably fibromyalgia, are in the form of tablets, capsules or sachets containing free DAO in powder, lyophilised powder, microcapsules, nanocapsules or liposomes of DAO with gastric protection.

The different compositions comprising DAO may also contain caffeine to potentiate the effects of prevention and treatment of the symptoms and disorders caused by fibromyalgia or chronic fatigue syndrome, preferably fibromyalgia.

Caffeine is an alkaloid of the xanthine group that has vasoconstriction capacity. Histamine produces vasodilation and this vasodilation produces pain. Caffeine contributes to vasoconstriction and therefore to alleviate the pain.

The DAO content in compositions of the present invention is between 0.1 and 50 mg per dose, preferably between 2 and 20 mg.

The caffeine content in the compositions of the present invention is between 1 and 100 mg per dose, preferably between 5 and 50 mg.

Compositions comprising DAO for use in the prevention and treatment of the symptoms and disorders caused by fibromyalgia or chronic fatigue syndrome, preferably fibromyalgia, can be taken before, after or with meals.

The use of compositions comprising DAO of the present invention directly affects the histamine level in blood and therefore the symptoms and disorders caused by fibromyalgia or chronic fatigue syndrome, preferably fibromyalgia, as a consequence of accumulated histamine levels.

The compositions of the present invention are prepared from free DAO, in powder, lyophilised powder, microcapsules, nanocapsules or liposomes of DAO that have an enteric coating layer that protects the DAO from gastric acidity, so that the different forms can be packaged directly in sachets or put into a capsule or compressed to give tablets. The enteric coating layer that coats the different forms rapidly disintegrates or dissolves in a neutral or alkaline medium.

In the case of microgranules, the cores can be inert cores based on sugar or similar base over which the DAO is applied or these cores can already contain DAO mixed with other excipients. These excipients can be binders, surfactants, filling materials, disintegrants, alkaline additives or other pharmaceutically acceptable ingredients either alone or in a mixture. The binders can be cellulose in type such as hydroxypropyl methylcellulose, hydroxypropyl cellulose and sodium carboxymethyl cellulose, polyvinylpyrrolidone, sugars, starches and other pharmaceutically acceptable substances with cohesive properties. Suitable surfactants can be from the groups of ionic or non-ionic acceptable surfactants such as, for example, sodium lauryl sulphate.

Alternatively, DAO can be mixed with alkaline compounds and additionally mixed with constituents suitable for formulation in a core material. These core materials can be produced by extrusion/spheronization or by compression using different processing equipment.

DAO can also be mixed with other pharmaceutically acceptable alkaline substances such as salts of phosphoric acid and sodium, potassium, calcium, magnesium and aluminium, carbonic acid, citric acid or other suitably weak organic or inorganic acids; a co-precipitate of aluminium hydroxide/sodium bicarbonate; substances normally used in anti-acid preparations such as aluminium, calcium and magnesium hydroxides; magnesium oxide or compound substances such as $Al_2O_3 \cdot 6MgO \cdot CO_2 \cdot 12H_2O$, $(Mg_6Al_2(OH)_{16}CO_3 \cdot 4H_2O$, $MgO \cdot Al_2O_3 \cdot 2SiO_2 \cdot nH_2O$ or similar compounds; pH buffering substances such as tris(hydroxymethyl)aminomethane, basic amino acids and their salts or other pharmaceutically acceptable pH buffering substances.

The enteric coating layers can contain pharmaceutically acceptable plasticizers to obtain the desired mechanical, flexibility and hardness properties. These plasticizers can be, for example, triacetin, citric acid esters, phthalic acid esters, cetyl alcohol, polyethylene glycols, polysorbates or other plasticizers.

The present invention also refers to a composition that comprises DAO according to any of the embodiments of the present invention for use in the prevention or treatment of the symptoms and disorders caused by fibromyalgia or chronic fatigue syndrome, preferably fibromyalgia.

The present invention also refers to a method of treatment that comprises administrating a composition comprising DAO, according to any of the embodiments of the present invention, to a patient who presents symptoms and disorders caused by fibromyalgia or chronic fatigue syndrome, preferably fibromyalgia, or who is at risk from suffering from them, in a therapeutically effective amount.

EXAMPLES

Example 1

Tablets of DAO were prepared from microgranules containing 4% DAO in accordance with the following formula:

| | |
|---|---|
| DAO | 4 mg |
| Mannitol | 40 mg |
| Microcrystalline cellulose | 25 mg |
| Hydroxypropyl cellulose | 10 mg |
| Maize starch | 10 mg |
| Citric acid | 6 mg |

The microgranules were coated with hydroxypropyl methylcellulose.

To make the tablets, the DAO microgranules were compressed with microcrystalline cellulose and sodium stearyl fumarate.

Example 2

Tablets of DAO were prepared from microgranules containing 4% DAO and 10% caffeine in accordance with the following formula:

| | |
|---|---|
| DAO | 4 mg |
| Caffeine | 10 mg |
| Mannitol | 35 mg |
| Microcrystalline cellulose | 15 mg |

-continued

| | |
|---|---|
| Hydroxypropyl cellulose | 10 mg |
| Hydroxypropyl methylcellulose | 10 mg |
| Ascorbic acid | 6 mg |

The microgranules were coated with a methacrylic acid copolymer.

To make the tablets, the DAO microgranules were compressed with microcrystalline cellulose and magnesium stearate.

Example 3

DAO sachets were prepared containing 100 or 150 mg of DAO microgranules prepared according to the first part of example 1.

Example 4

DAO and caffeine sachets were prepared containing 100 or 150 mg of DAO microgranules prepared according to the first part of example 2.

Example 5

DAO capsules were prepared containing 100 or 150 mg of DAO microgranules prepared according to the first part of example 1, filling the soft gelatine capsules with the microgranules.

Example 6

DAO and caffeine capsules were prepared containing 100 or 150 mg of DAO microgranules prepared according to the first part of example 2, filling the soft gelatine capsules with the microgranules.

Example 7

Determination of the efficacy of DAO compositions, which are an object of the present invention, in subjects diagnosed with fibromyalgia and who showed a deficit of DAO.

Oral compositions containing DAO, alone or associated with caffeine, which are an object of the present invention, were tested in a total of 65 subjects diagnosed with fibromyalgia, as out-patients.

Before assigning the subjects to the study, levels of histamine in blood were measured as well as the activity level of DAO in plasma. Those subjects with blood histamine values over 20 micrograms per decilitre and levels of DAO activity below 40 HDU/mL were included in the study.

After the first analysis, there were 42 selected subjects (38 women and 4 men, of ages between 21 and 45 years) who were randomly assigned DAO compositions or placebo.

The following tables show the results in relation to the reduction of symptoms and disorders caused by fibromyalgia after the administration of a dose protocol of 4 mg DAO twice a day in 21 subjects diagnosed with fibromyalgia and with DAO deficit in comparison with 21 subjects who were administered placebo.

TABLE 1

Comparative results of the symptoms and disorders caused by fibromyalgia between subjects taking DAO tablets, of Example 1, and those not taking DAO.

| Symptoms and disorders of fibromyalgia | Subjects taking DAO: 21 | Subjects not taking DAO: 21 |
|---|---|---|
| Back pain | 3 of 21 | 20 of 21 |
| Lumbar pain | 4 of 21 | 19 of 21 |
| Neck pain | 4 of 21 | 20 of 21 |
| Knee pain | 5 of 21 | 21 of 21 |
| Fatigue | 5 of 21 | 21 of 21 |
| Histamine level in blood | 2-20 micrograms/0.1 L | >>20 micrograms/0.1 L |

The degree of pain, both in the initial diagnosis of fibromyalgia and in monitoring the group treated with DAO and the placebo group, was determined using the McGill pain scales for measuring pain quality and the visual analogue scale (VAS) for measuring pain intensity.

The McGill pain questionnaire, which enables measurement of pain quality, is a questionnaire where the patient must choose a descriptor for each scale best representing their pain experience, deciding if the pain is throbbing, pulling, sharp, etc. and a second category measuring the emotional component where the patient describes the pain choosing between adjectives such as "tiring", "punishing" or "wretched", etc.

The Visual Analogue Scale (VAS) is the most commonly used instrument in clinical studies to evaluate the pain intensity of fibromyalgia. The patient is shown a horizontal or vertical line with the ends marked for the absence of pain and the worst possible or imaginable pain; they are asked to mark a point on the line reflecting their pain, and then the distance in millimetres from the no pain end to the point marked by the patient is measured.

"Pain maps" were also used to determine the location and spatial extension of the symptom; however, the maps are only an aid and do not replace a good clinical evaluation. Normally, a map is used with sensitive points for fibromyalgia, where serial evaluation of whether the pain reduces or increases can be evaluated in successive measurements in each of these points. These maps are very useful for monitoring pain.

Pain measurement tests were also based on tolerance to pressure applied at the point affected by the pain using a rubber probe. Patients with fibromyalgia require much less pressure to activate the neurones associated with acute pain in the brain than healthy patients. The magnitude of pain, sensitivity to pain and symptoms of depression were compared in the subjects using an exploratory scanner (MRI).

TABLE 2

Comparative results of the symptoms and disorders caused by fibromyalgia between subjects taking DAO and caffeine tablets, of Example 2, and those not taking DAO and caffeine. Subjects selected for this trial were diagnosed with fibromyalgia but without associated sleep disorders.

| Symptoms and disorders of fibromyalgia | Subjects taking DAO and caffeine: 21 | Subjects not taking DAO and caffeine: 21 |
|---|---|---|
| Cephalea | 2 of 21 | 20 of 21 |
| Fatigue | 4 of 21 | 21 of 21 |

TABLE 2-continued

Comparative results of the symptoms and disorders caused by fibromyalgia between subjects taking DAO and caffeine tablets, of Example 2, and those not taking DAO and caffeine. Subjects selected for this trial were diagnosed with fibromyalgia but without associated sleep disorders.

| Symptoms and disorders of fibromyalgia | Subjects taking DAO and caffeine: 21 | Subjects not taking DAO and caffeine: 21 |
|---|---|---|
| Histamine level in blood | 2-20 micrograms/0.1 L | >>20 micrograms/0.1 L |

Example 8

Determination of the efficacy of DAO compositions of the present invention in subjects diagnosed with chronic fatigue syndrome and who showed a deficit of DAO.

Oral compositions containing DAO of the present invention were tested in a total of 46 subjects diagnosed with chronic fatigue syndrome, as out-patients.

To evaluate the degree of affectation of chronic fatigue syndrome in candidate study subjects, the quality of life of these subjects was evaluated using a simple scale of 4 successive grades (I, II, III and IV), with criteria used in the clinic. This scale is used in the Chronic Fatigue Syndrome (CFS) Functional Unit in the Hospital Clinic.

The CLINIC scale consists of dividing the patients with chronic fatigue syndrome into four different grades of functional affectation depending on the effect of their fatigue on quality of life:

GRADE I: the patient is sometimes or occasionally fatigued, without significant limitation (<50%) of work or daily life activities.

GRADE II: persistent presence of fatigue, oscillating but without improvement, with marked effect (>50%) on work and also daily life activities.

GRADE III: marked fatigue that does not allow, even occasionally, performing any type of work, which limits autonomy and activities of daily life by more than 80%.

GRADE IV: extreme fatigue that requires the help of other people for basic personal activities and that makes autonomy and the activities of daily life impossible.

Improvement is evaluated when the patient passes from a higher to a lower grade in terms of the number of improvement grades.

The following table shows the results in relation to the number of grades of improvement on the CLINIC scale in 23 subjects diagnosed with chronic fatigue syndrome of grades II, III and IV and with DAO deficit, after the administration of a dose protocol of 4 mg DAO twice a day in comparison with 23 subjects administered placebo.

| Number of grades of improvement | Subjects taking DAO: 23 | Subjects not taking DAO: 23 |
|---|---|---|
| 1 | 16 of 23 | 2 of 23 |
| 2 | 4 of 23 | 0 of 23 |
| Histamine level in blood | 2-20 micrograms/0.1 L | >>20 micrograms/0.1 L |

What is claimed is:

1. A method of treating a patient,
   wherein the patient presents the symptoms and disorders caused by fibromyalgia or chronic fatigue syndrome,
   wherein the symptoms and disorders comprise fatigue, sleep disorders and musculoskeletal pain,
   wherein the method comprises administering to said patient a composition comprising diamine oxidase (DAO), and
   wherein the administering results in a treatment of the patient, wherein the treatment is characterized by an effect selected from the group consisting of relief from the symptoms and disorders of fibromyalgia or chronic fatigue syndrome, reduction of any direct or indirect pathology of fibromyalgia or chronic fatigue syndrome, reduction of the speed of progression of fibromyalgia or chronic fatigue syndrome, improvement of fibromyalgia or chronic fatigue syndrome, prevention of recurrence of fibromyalgia or chronic fatigue syndrome, or combinations thereof.

2. The method according to claim 1, wherein said DAO is administered orally in the form of tablets, capsules or sachets.

3. The method according to claim 1, wherein said DAO is administered at a dose of between 0.1 and 50 mg.

4. The method according to claim 1, wherein said composition also contains caffeine.

5. The method according to claim 1, wherein said composition also contains caffeine which is administered at a dose of between 1 and 100 mg.

6. The method according to claim 1, wherein said DAO has a gastric protection.

7. The method according to claim 1, wherein said DAO is used in free form, in powder, lyophilised powder, microcapsules, nanocapsules or liposomes.

* * * * *